(12) United States Patent
Johnson et al.

(10) Patent No.: US 8,133,919 B2
(45) Date of Patent: *Mar. 13, 2012

(54) DRY FERTILIZER WITH GROWTH HORMONE-CONTAINING FORMULATION AND METHODS OF USE AND MAKING

(75) Inventors: Louis B. Johnson, Troy, AL (US); Jeffery L. Peel, Malvern, AL (US)

(73) Assignee: Accelegrow Technologies, Inc., West Point, GA (US)

( * ) Notice: Subject to any disclaimer, the term of this patent is extended or adjusted under 35 U.S.C. 154(b) by 437 days.

This patent is subject to a terminal disclaimer.

(21) Appl. No.: 12/285,729

(22) Filed: Oct. 14, 2008

(65) Prior Publication Data

US 2009/0048107 A1 Feb. 19, 2009

Related U.S. Application Data

(63) Continuation of application No. 11/826,458, filed on Jul. 16, 2007, now abandoned, which is a continuation-in-part of application No. 11/701,510, filed on Feb. 2, 2007, now abandoned, which is a continuation-in-part of application No. 11/211,424, filed on Aug. 26, 2005, now abandoned.

(51) Int. Cl.
*A61K 31/04* (2006.01)
*A61K 9/00* (2006.01)
*A01N 33/18* (2006.01)
*A01N 33/24* (2006.01)

(52) U.S. Cl. .......... 514/740; 514/970; 424/400

(58) Field of Classification Search .......... 514/740, 514/970; 424/400

See application file for complete search history.

(56) References Cited

U.S. PATENT DOCUMENTS

| | | | |
|---|---|---|---|
| 4,224,048 A | 9/1980 | Pendergast | |
| 4,647,637 A | 3/1987 | Tschang et al. | |
| 4,670,039 A | 6/1987 | Sjogren | |
| 4,816,568 A * | 3/1989 | Hamilton et al. | 530/399 |
| 5,201,930 A | 4/1993 | Campbell | |
| 6,339,043 B1 * | 1/2002 | Kirby et al. | 504/234 |
| 6,458,546 B1 | 10/2002 | Baker | |
| 6,500,223 B1 | 12/2002 | Sakai et al. | |
| 2002/0053229 A1 | 5/2002 | Varshovi | |
| 2005/0123499 A1 * | 6/2005 | Majmudar | 424/74 |
| 2005/0288188 A1 | 12/2005 | Volgas et al. | |

* cited by examiner

*Primary Examiner* — Johann Richter
*Assistant Examiner* — Mei-Ping Chui
(74) *Attorney, Agent, or Firm* — Clark & Brody

(57) ABSTRACT

A growth hormone formulation includes an enzyme inactivating component and a preservative. The formulation can be incorporated into a dry fertilizer for application using the fertilizer itself or a component of the fertilizer such as one or more of the fillers commonly used in fertilizers.

23 Claims, No Drawings

DRY FERTILIZER WITH GROWTH HORMONE-CONTAINING FORMULATION AND METHODS OF USE AND MAKING

This application is a continuation of application Ser. No. 11/826,458 filed Jul. 16, 2007 now abandoned, which is a continuation-in-part of application Ser. No. 11/701,510, filed on Feb. 2, 2007 now abandoned, which is a continuation-in-part of application Ser. No. 11/211,424 filed on Aug. 26, 2005 now abandoned, which is incorporated herein by reference, which claims the benefit of provisional application No. 60/610,202 filed on Sep. 16, 2004.

TECHNICAL FIELD

The present invention relates to a growth hormone-containing formulation and a method of making, and in particular to a formulation for use with fertilizers that are designed to be applied in dry form.

BACKGROUND ART

Kelp, commonly referred to as seaweed, grows along coastlines around the world and is botanically classified as algae. The use of liquid kelp as a growth stimulant is well known in the agricultural industry. This seaplant is rich in micronutrients and natural growth hormones, including cytokinins, auxins and gibberellins, which stimulate cell division and larger root systems. Kelp extracts can be applied as a foliar spray on plants and the like, or on soil for later contact and absorption by root structures. An extract applied to land plants is known to accelerate growth, increase fruiting and flowering, intensify color, and provide resistance to disease, insects, drought, and frost. Many commercial liquid formulations of kelp are available for use in the agricultural industry and can be found in various retail and wholesale outlets, as well as through the internet. These kelp formulations are basically an extract of kelp diluted with water, and may contain other components as the manufacturer of the formula may see fit. Examples of formulations include those sold at the Gardens Alive website www.gardensalive.com, Sea Crop Liquid Kelp Extract (to be diluted in water), and the like.

It is also known to use kelp in tablet or capsule form to treat different health problems. One problem with present day liquid kelp materials is the short shelf life of the formulation. When the kelp is combined with water and other components, bacteria or other impurities present in the water or other additives break down the growth hormones found in the kelp, thus rendering them ineffective over time.

Thus, a need exists to provide improved kelp formulations, including those that have extended shelf lives. The present invention responds to this need by providing a liquid kelp formulation that has an increased shelf life.

SUMMARY OF THE INVENTION

One object of the present invention is an improved dry growth hormone-containing formulation.

Another object of the invention is a method of making the dry growth hormone-containing formulation.

Other objects and advantages will become apparent as a description thereof proceeds.

In satisfaction of the foregoing objects and advantages, one aspect of the invention is an improvement in liquid kelp formulations by the presence of an effective amount of an enzyme inactivating component selected from the group consisting of sarcosine, manganese chloride, sodium dodecyl sulfate, sodium lauryl sarcosinate, grape seed oil, pine bark extract, grape leaf, black currant, passion flower, and chlorella vulgaris to reduce the degradation of growth hormones in the liquid kelp formulation. A preservative is also included, the preservative amount effective to retard growth of bacteria, fungi, and/or mold in the liquid kelp formulation. The enzyme inactivating component preferably ranges from zero and up to 5.0% by weight of the formulation, more preferably between 0.25% and 3.0%, and most preferably between 0.5, to 1.5%. A preferred enzyme inactivating component is sarcosine.

The preservative is preferably a food grade preservative and/or the preservative is in a range of from 0.10, to 1% by weight, more preferably between 0.15% and 0.5%, and most preferably around 0.2-0.3%. The preservative is preferably one of methyl paraben, propyl paraben, and diazolidinyl urea.

The formulation can also include an effective amount of a surfactant for wetting purposes, preferably a nonionic surfactant such as an alcohol ethoxylate. The alcohol ethoxylate preferably has 9, or more moles of ethoxylation.

The formulation can also include a source of nitrogen, phosphorous, or potassium, and if nitrogen is used, it is preferred to use a compound containing ammonia or urea.

The invention entails the method of using the formulation wherein the liquid kelp formulation is applied to plant, for example, by direct application to the plants themselves, including to the foliage and/or roots of the plants, and to the soil in the vicinity of the plants.

Another aspect of the invention entails improvements in the method of applying a liquid kelp formulation to plants. In this aspect, the kelp is provided into a solid form, made into a solution, and immediately applied to plants or soil. This method can be modified by including the enzyme inactivating component and/or preservative discussed above. The enzyme inactivating component and/or preservative can be present as part of either the solid kelp or the water prior to the adding step. In another alternative, the enzyme inactivating component and/or preservative could be maintained as separate components and added either individually or together to either the water or a water-kelp solution.

The invention also entails the use of synthetic growth hormones in place of or with the natural hormones found in kelp. In this embodiment, the kelp can be replaced with or combined with synthetic growth hormones for treating plants, seeds, and the like. The synthetic growth hormone-containing formulation can be applied to seeds, plants, etc, in a similar manner as disclosed for the formulation containing kelp.

One further aspect of the invention is the combination of the growth hormone-containing formulation with a dry fertilizer. In contrast to the liquid versions of the growth hormone-containing formulation, this embodiment incorporates the formulation into a dry fertilizer so that it can be used as such. For example, the growth hormone-containing formulation could be combined with the dry fertilizer such that it coats the fertilizer in its final product form. Another option is to incorporate the growth hormone-containing formulation into a component of the fertilizer such as a filler. Other options include incorporation of a dry growth hormone-containing formulation into the fertilizer or a component thereof, or the incorporation of dry and liquid portions making up the growth hormone-containing formulation into the fertilizer.

Incorporation of the growth hormone-containing formulation into such a component can be done in any number of ways, coating, mixing, or any other process that would allow the growth hormone-containing formulation to be combined with the filler so that the filler acts as a carrier for the growth hormone-containing formulation in the overall fertilizer composition. Examples of fillers include sodium sulphate, talc, clay, calcium carbonate, bentonite, silica, diatomaceous earth, metal oxides such as titanium oxide, sulfur powder, water swellable polymers, and slow release agents such as resins, gypsum cements, and carbon as suggested in U.S. Pat. No. 4,670,039, to Sjogren, which is herein incorporated by reference in its entirety. This list is only exemplary and any fillers known for use in fertilizers can be employed with the growth hormone-containing formulation so that it can be used in a dry form rather than a liquid form.

The manner of incorporation of the growth hormone-containing formulation into the filler can also vary. Known methods such a coating, mixing, immersion, wherein the filler is either in final form or the growth hormone-containing formulation is incorporated as part of filler formation.

DESCRIPTION OF THE PREFERRED EMBODIMENTS

The present invention is an improvement over the kelp formulations found in the prior art. By practicing the invention, the breakdown of the growth hormones found in kelp is slowed or eliminated as a result of additives combined with the kelp or the manner in which the kelp is combined with water and additives.

The liquid kelp formulation or system of the invention can be applied to plants or any vegetation that would require a boost in growth or benefit from other effects attributable to kelp. The term "plants" is intended to encompass any and all vegetation in this regard that would benefit from application of kelp. Examples includes vegetables, legumes, flowers, shrubs, trees, grasses, fruits, vines, etc., and their roots in the event that the formulation is used as a root dip or applied to soil to improve root structure. The inventive formulation could also be employed to treat seeds, e.g., coating or treating the seeds with the formulation by spraying, immersing, or the like.

In one embodiment of the invention, an additive-containing kelp formulation is made that has extended shelf life, and can then be used at a later time to stimulate growth in plants and the like.

In another embodiment, a system is provided that produces an aqueous liquid formulation, with or without various additives. As part of this system, the kelp is maintained separately from liquid formulation until the formulation as made is to be applied in a given manner. The kelp, in virtually any solid form, can be added to the aqueous liquid formulation. The formulation can contain additives when combined with the kelp, can be additive free, or can have the additives added after kelp addition. For example, the solid form of the kelp could be a capsule, a pellet, granule, tablet, meal, or other solid form. The additives can be those employed with the liquid formulation of the invention, or other known additives that are commonly found in kelp formulations.

Turning to the liquid kelp formulation aspect of the invention, one additive is an enzyme inactivating component such as sarcosine, manganese chloride, sodium dodecyl sulfate, sodium lauryl sarcosinate, grape seed oil, pine bark extract, grape leaf, black currant, passion flower, and chlorella vulgaris with sarcosine being a preferred enzyme inactivating component. An effective amount is employed in the liquid kelp formulation such that the growth hormones therein do not break down as fast over time as they would without the inactivating additive. A more preferred amount is up to 5.0% by weight of the total formulation, with more preferred ranges between 0.25, and 3.0%, and most preferably between 0.5, to 1.5%. Enzyme inactivating compounds are disclosed in U.S. Pat. No. 6,458,546 to Baker et al. (Baker), which is herein incorporated in its entirety by reference. It should be noted that the Baker patent references SARKOSYL as one of the enzyme inactivating ingredients. SARKOSYL is actually a trademark, and the proper chemical reference is sarcosine, as noted in Hawley's The Condensed Chemical Dictionary, Eighth Edition, pp. 774 and 775. The chemical name for sarcosine is methyl glycocoll aminoacetic acid. The Baker patent is not relevant to the present invention and is concerned with the preservation of DNA in samples, and discloses the addition of the enzyme inactivating components in combination with a divalent metal chelator such as EDTA, EGTA, and BAPTA, and at least one chelator enhancing component such as lithium chloride, guanidine, sodium salicylate, sodium perchlorate, and sodium thiocyanate, each in specified amounts. It is contemplated that the chelator and chelator-enhancing component of Baker could be employed with the effective amount of the enzyme inactivating components that is utilized in the present invention if so desired, and in the amounts taught by Baker.

Another additive for the liquid kelp formulation is a preservative in an amount effective to preserve the formulation and resist bacterial, fungi, and/or mold growth. Preferred ranges include from 0.10, to 1% by weight, more preferred ranges include 0.15% to 0.5% with a target of around 0.2-0.3%. Virtually any known preservative can be employed in the formulation, with examples including those using propyl paraben, methyl paraben, and diazolidinyl urea, e.g., Germaben II. Another specific preservative that can be used is Dantoguard® manufactured by Lonza, see www.Lonza.com. Dantoguard® Plus is another preservative adaptable for use in the invention, this particular preservative more adapted for battling fungi and bacteria.

Since the kelp could be sprayed on food bearing plants, it is important to ensure that the additives are food safe. In this regard, if the liquid kelp is intended to be sprayed on plants or other vegetation or come into contact with any vegetation that may be eaten or bear fruit, the preservative should be a food grade preservative such as the methyl or propyl parabens mentioned above.

If so desired, the kelp formulation could be enhanced with additional fertilizing additives or agents that provide nitrogen, phosphorous, or potassium, or other micronutrients such as those containing trace elements like boron, selenium, zinc, and the like. One example would be an amount of ammonia to provide additional nitrogen. The amount should be sufficient to have an effect on the treated plants, with a preferred amount being up to about 10.0% by weight of the formulation, and more preferably 5-10% by weight. One example would be a formulation of 3-3-3, of nitrogen, phosphorous and potassium.

One example of a preferred formulation is as follows:

| Component | Percentage by weight | 55 gallons (in lbs. except for water) | 5 gallons (in lbs.) |
|---|---|---|---|
| Powdered kelp | 5.0 | 23 | 2.0 |
| Nipasol-m-sodium[1] | 0.3 | 1.4 | 0.1 |
| Ammonia[2] | 0.5% | 2.3 | 0.2 |
| Sarcosine | 1.0 | 4.6 | 0.4 |
| Water | 93.2 | 51 gallons | 37.2 |

[1]Nipasol-m-sodium is a propyl paraben preservative.
[2]Ammonia is added as an additional fertilizer boost.
Another preservative that could be used as part of the formulation is Nipacide Bit-20, made by Clariant Corporation of Charlotte, N.C. While ammonia is exemplified here, other fertilizers such as urea could be used.

In formulating the liquid kelp, it is preferred to dissolve the preservative into the water first while taking the necessary precautions to avoid inhaling any of the preservative, and then add the remaining components, although the components could be added in any order if so desired.

The liquid kelp formulation can be made in a concentrated form which would be diluted by the end user, or in a ready to use concentration as exemplified by the table above, with either of these modes of delivery well known in the art. When making a concentrate, the weight percentages of the various additives would be adjusted so that when the concentrate is diluted, the percentages still fall within the ranges given above for the broad and more preferred embodiments of the invention.

The manner of application of the liquid kelp formulation can be any type known in the art. For example, the formulation can be used as a foliar spray, or for dipping plant roots, or applied directly to soil so that the formulation can interact with roots of the plants in the soil, or for treating seeds such as by coating, immersion, or the like.

It should also be understood that the formulation can include one or more surfactants for wetting if so desired. When using a surfactant, virtually any surfactant that imparts wetting to the formulation can be used. A preferred class of surfactants includes nonionic types such as alcohol ethoxylates, with preferred moles of ethoxylation being about 9, or more.

The kelp can be obtained from any commercial source of kelp for use in the invention, either in making the liquid kelp formulation or a solid form for later dissolution and use.

As mentioned above, another aspect of the invention is a system entailing making of a liquid kelp formulation by providing a solid form of kelp and dissolving it in water. The water can contain other additives as desired. Alternatively, the kelp in solid form could contain the additives, as desired. The additives can be those known in the art such as fertilizing additives, or the additives noted above.

In an alternate mode of this aspect of the invention, the additives could be separate from the water and solid kelp and added to the water, either before or after dissolving the kelp. This system of the invention is advantageous in that the kelp is kept separate from the water and its impurities until it is desired to apply the kelp to a given plant or area. Thus, a potent kelp liquid is provided that does not suffer from potency loss like liquid kelps that have been stored over time do. The form of the solid kelp can be any type, e.g., tablet, pill, capsule, powder, granule, pellet, cake, or the like. The form of the additives can also be any type, liquid or solid. As noted above, the additives can be any type typically found in known kelp formulations or they can include those mentioned above in terms of the enzyme inactivating component, preservative, and/or surfactant and fertilizer. It is anticipated that the enzyme inactivating component may be optional in this mode of the invention since the kelp would be used immediately after forming the liquid, and the breakdown of growth hormones would not be the significant problem that it is with prior art kelp liquids. The preservative may also be optional, but could be added to the solid kelp to preserve its shelf life.

Another embodiment of the invention entails the use of the enzyme inactivating component in combination with a formulation containing a synthetic growth hormone instead of the above-mentioned liquid or solid kelp formulation that contain natural growth hormones such as cytokinins, auxins, and gibberellins. One example of these synthetic growth hormones is Technical Kinetin, which is sold as 98.5, wt. % cytokinin and 1.5, wt. % other ingredients, and is available from Stoller USA of Houston Tex. Other materials from Stoller USA that are synthetic growth hormones include Technical Gibberellic Acid ($GA_3$), which contains 92, wt. % of gibberellic acid and 8, wt. % other ingredients material, and Indole-3-butyric Acid, which contains 99, wt. % indole-3-butyric acid (auxin) and 1, wt. % other ingredients. Other synthetic growth hormones include abscisic acid (ABA), jasmonic acid, ethylene, 1-naphthylacetic acid (NM) brassinosteriods, salicylic acid (SA), oligogalacturonides (pectin-derived polymers), xyloglucan (hemicellulose-derived polymers), and benzyladenine (BA). It should be understood that the Stoller USA products and those recited above are only examples of the types of synthetic hormones that can be employed and others that are commercially available are also within the scope of the invention.

The synthetic growth hormone can be used with the enzyme inactivating component and preservative in any number of ways. The synthetic growth hormone is normally provided in liquid form can be combined with the enzyme inactivating component and preservative and sprayed or otherwise applied to the intended material for treatment. If the synthetic growth hormone is in solid form such as a powder, it can be combined with the enzyme inactivating component and preservative formulation and then made into a solution or added to a solution containing the enzyme inactivating component and preservative. In addition, the synthetic growth hormones can also be employed in the same manner as described above for the kelp in both solid and liquid forms.

Using synthetic growth hormones in substitution of kelp offers the advantages that the possible contaminants in kelp are avoided, and supply problems which may occur since kelp must be harvested can be eliminated. Since kelp has filtering properties when it is in water, it can take up unwanted materials such as heavy metals due to ocean pollution. While there are ample sources of kelp and the contamination of kelp is not believed to be a severe problem, using synthetic hormones eliminates any risk of the presence of unwanted materials in the kelp. Also, since the supply of kelp could be disrupted to do economic or natural events, its availability can fluctuate. The manufacture of synthetic growth hormones is not subject to such influences, and it can always be readily available if needed.

As yet another embodiment, the synthetic growth hormones could be combined with the kelp when using the enzyme inactivating component and preservative if so desired. The weight ratio of the two could vary from just a minor amount of synthetic growth hormone, e.g., less than 1, percent, to a predominance of the synthetic growth hormone, e.g., greater than 99%.

Another embodiment of the invention involves the growth hormone-containing formulation in dry form. The aim of this embodiment is to be able to apply the growth hormone-containing formulation, whether using a natural or synthetic hormone and the enzyme inactivating component and preservative in a dry form, rather than a liquid spray or the like as described above.

The dry application of the growth hormone-containing formulation may take on a number of modes. A first mode would be to coat a fertilizer with the liquid growth hormone-containing formulation, much like fertilizers are coated with herbicides for weed killing. The coating process could be any type known in the art, such as spraying the fertilizer with the growth hormone-containing formulation, immersing, etc., and then packaging the coated fertilizer for use in a given application.

A second mode would be to combine the liquid growth hormone-containing formulation with a filler that is commonly used in fertilizer, and then combine the filler with the fertilizer for dry use. Typical fertilizer fillers include sodium sulphate, talc, clay, calcium carbonate, bentonite, silica, diatomaceous earth, metal oxides such as titanium oxide, sulfur powder, etc. Combining the growth hormone-containing formulation with the filler can also be done in any known fashion, e.g., coating the filler by spraying, immersion techniques and the like.

Another class of fillers can be water swellable polymers. These types of polymers are disclosed in U.S. Pat. No. 4,224,048, to Pendergast, herein incorporated by reference. In the Pendergast patent, a fertilizer is shown impregnated within a water swellable polymer. The polymer absorbs water administered to the plant, dilutes fertilizer into the water and passes the water/fertilizer solution on to the plant with a controlled capillary action. Another example of using a water swellable polymer is U.S. Pat. No. 4,647,637, to Tschang et al., herein incorporated by reference. These polymers which are only slightly swellable are used as adsorbents or formulation assistants for fertilizers. According to the invention, the growth hormone-containing formulation can be incorporated into these types of water swellable polymers and the polymers can be used as filler for fertilizer. The incorporation can be done in any known way, spraying or coating the growth hormone-containing formulation onto the polymers or incorporating the growth hormone-containing formulation into the structure of the water swellable polymers.

In yet another mode, the growth hormone-containing formulation can be combined with the fertilizer using dry technique or combination of dry and liquid techniques.

For a dry technique, the components of the growth hormone-containing formulation can be used in dry form, i.e., the growth hormone, the sarcosine, and the preservative could be combined together and this combination then combined with the desired fertilizer, filler or mix thereof. Alternatively, the dry components of the growth hormone-containing formulation could be directly combined with the fertilizer and/or filler. In essence, any order of combination can be employed when combining the various dry components together to make the final dry fertilizer formulation.

The mode of liquid and dry techniques can involve preparing one or more of the components of the growth hormone-containing formulation in liquid form with others in dry form. For example, the enzyme inactivating component, e.g., sarcosine, could be made into a solution and combined with the other dry components as the growth hormone, natural or synthetic and fertilizer/filler. The solution could also include the sarcosine and preservative with the other dry components. Given the differences in percentage amounts, a preferred way of incorporation of the growth hormone-containing formulation into the fertilizer is to add the enzyme-inactivating component by way of solution, since this affords more uniformity in the distribution of the enzyme inactivating component as compared to its addition in a dry mode, which would require sufficient mixing to ensure an even distribution. Again, though it should be understood that the sequence of combining the various components can vary to produce the final dry fertilizer formulation.

The dry fertilizer can be applied in any known way to existing plants such as trees, shrubs, vegetables, grass, flowers and the like, or seeds or roots or virtually anything that requires fertilization. Moreover, any type of dry fertilizer is believed to be adaptable for this aspect of the invention. The fertilizer/filler may be in granular form which would be ideal for accepting a coating of the growth hormone-containing formulation, or a mix of fertilizer and a filler such as a water swellable polymer. The fertilizer could be in powder form, tablet form, or any form commonly employed to provide the fertilizing nutrients to a plant, seed, root, or the like.

While a number of fertilizers are discussed above, another example of a dry fertilizer is a slow release fertilizer incorporating a slow release agent such as those disclosed in aforementioned U.S. Pat. No. 4,670,039, to Sjogren. These types of fertilizers include some type of a slow release agent like a resin or the combination of a gypsum cement and carbon particles that break down slowly over time to allow for a gradual release of the fertilizer to the intended plants, roots, seeds or the like. As with the other embodiments, the growth-hormone-containing formulation can be incorporated into the fertilizer or filler or combination thereof of these types of fertilizers for timed release, either using the all liquid approach, all dry approach, or combination of dry and liquid techniques.

As such an invention has been disclosed in terms of preferred embodiments thereof, which fulfills each and every one of the objects of the invention as set forth above, and provides a dry fertilizer formulation containing a growth hormone-containing formulation and method of use.

Of course, various changes, modifications and alterations from the teachings of the present invention may be contemplated by those skilled in the art without departing from the intended spirit and scope thereof. It is intended that the present invention only be limited by the terms of the appended claims.

We claim:

1. In a dry fertilizer formulation having fertilizer and filler components, the improvement comprising a growth hormone-containing formulation incorporated with the dry fertilizer formulation, wherein the growth hormone-containing formulation comprises a growth hormone to stimulate growth in plants, an effective amount of sarcosine as an enzyme inactivating component to reduce the degradation of growth hormones in the growth hormone-containing formulation, and a preservative in an amount effective to retard growth of bacteria, fungi, and/or mold in the growth hormone-containing formulation.

2. The formulation of claim 1, wherein the enzyme inactivating component ranges up to 5.0% by weight of the growth hormone-containing formulation.

3. The formulation of claim 2, wherein the enzyme inactivating component ranges between 0.25 and 3.0% by weight of the growth hormone-containing formulation.

4. The formulation of claim 1, wherein the preservative is a food grade preservative.

5. The formulation of claim 4, wherein the preservative is in the range of from 0.10 to 1.0% by weight of the growth hormone-containing formulation.

6. The formulation of claim 1, further comprising an effective amount of a surfactant for wetting purposes.

7. The formulation of claim 1, wherein the growth hormone-containing formulation is coated onto the dry fertilizer formulation.

8. The formulation of claim 1, wherein the growth hormone-containing formulation is incorporated with the filler of the fertilizer.

9. The formulation of claim 8, wherein the growth hormone-containing formulation is coated onto the filler or is added to the filler.

10. The formulation of claim 8, wherein the filler is selected from the group consisting of sodium sulphate, talc, clay, calcium carbonate, bentonite, silica, diatomaceous earth, metal oxides, sulfur powder, a slow release agent, and water swellable polymers.

11. A method for plant growth stimulation, the improvement comprising applying a dry fertilizer formulation of claim 1 to plants, roots, seeds, or earth in the vicinity of the plants, roots or seeds.

12. The method of claim 11, wherein the dry fertilizer formulation is applied to the earth in the vicinity of the plants, roots, or seed.

13. A method of making a dry fertilizer formulation, comprising the step of incorporating a growth hormone-containing formulation of claim 1 with a dry fertilizer wherein the growth hormone-containing formulation is either in dry form, liquid form, or a mixture thereof.

14. The method of claim 13, wherein the growth hormone-containing formulation is in a liquid form when incorporated with the dry fertilizer.

15. The method of claim 13, wherein the dry fertilizer includes a filler.

16. The method of claim 15, wherein the filler is selected from the group consisting of sodium sulphate, talc, clay, calcium carbonate, bentonite, silica, diatomaceous earth, metal oxides, sulfur powder, a slow release agent, and water swellable polymers.

17. The method of claim 15, wherein the growth hormone-containing formulation is incorporated into the filler.

18. The method of claim 15, wherein the growth hormone-containing formulation is coated onto the filler or is added to the filler.

19. The formulation of claim 3, wherein the enzyme inactivating component ranges between 0.5 and 1.5% by weight of the growth hormone-containing formulation.

20. The formulation of claim 10, wherein the metal oxide is titanium oxide.

21. The formulation of claim 16, wherein the metal oxide is titanium oxide.

22. The formulation of claim 5, wherein the preservative is in the range of from 0.15 to 0.5% by weight of the growth hormone-containing formulation.

23. The formulation of claim 6, wherein the surfactant is a nonionic surfactant.

* * * * *

UNITED STATES PATENT AND TRADEMARK OFFICE
CERTIFICATE OF CORRECTION

| | |
|---|---|
| PATENT NO. | : 8,133,919 B2 |
| APPLICATION NO. | : 12/285729 |
| DATED | : March 13, 2012 |
| INVENTOR(S) | : Louis B. Johnson and Jeffery L. Peel |

Page 1 of 1

It is certified that error appears in the above-identified patent and that said Letters Patent is hereby corrected as shown below:

On the Title Page, Item [60] Related U.S. Application Data should be added to include U.S. Provisional Application No. 60/610,202, filed on September 16, 2004

Signed and Sealed this
Sixteenth Day of July, 2013

Teresa Stanek Rea
*Acting Director of the United States Patent and Trademark Office*